United States Patent [19]

Seele et al.

[11] Patent Number: 5,133,799
[45] Date of Patent: Jul. 28, 1992

[54] N-ARYLTETRAHYDROPHTHALIMIDES AND HERBICIDAL COMPOSITIONS THEREOF

[75] Inventors: Rainer Seele, Fussgoenheim; Lothar Rueb, Speyer; Reiner Kober, Fussgoenheim; Karl Eicken, Wachenheim; Karl-Otto Westphalen, Speyer; Bruno Wuerzer, Otterstadt, all of Fed. Rep. of Germany

[73] Assignee: BASF Aktiengesellschaft, Ludwigshafen, Fed. Rep. of Germany

[21] Appl. No.: 697,036

[22] Filed: May 8, 1991

[30] Foreign Application Priority Data

May 10, 1990 [DE] Fed. Rep. of Germany ....... 4015144

[51] Int. Cl.$^5$ .................. A01N 43/38; C07D 209/48
[52] U.S. Cl. ........................................... 71/92; 71/96; 548/266.4; 548/336; 548/374; 548/467
[58] Field of Search ................ 548/374, 336, 266.4, 548/467; 71/92, 96

[56] References Cited

U.S. PATENT DOCUMENTS

| | | | |
|---|---|---|---|
| 4,824,476 | 4/1989 | Pissiotas et al. | 71/95 |
| 4,917,721 | 4/1990 | Pissiotas et al. | 71/96 |
| 4,925,484 | 5/1990 | Rueb et al. | 71/96 |
| 4,937,354 | 6/1990 | Fischer et al. | 548/513 |

FOREIGN PATENT DOCUMENTS

| | | |
|---|---|---|
| 0207894 | 1/1987 | European Pat. Off. |
| 0337151 | 3/1989 | European Pat. Off. |
| 0319791 | 6/1989 | European Pat. Off. |
| 3815042 | 11/1989 | Fed. Rep. of Germany |

Primary Examiner—Mary C. Lee
Assistant Examiner—Jacqueline Haley
Attorney, Agent, or Firm—Keil & Weinkauf

[57] ABSTRACT

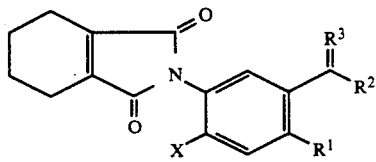

where
X is hydrogen or halogen;
$R^1$ is $C_1$–$C_4$-alkyl which may carry from one to five halogen atoms or one of the groups stated for X;
$R^2$ is a heteroaromatic structure bonded via a nitrogen atom, which has a 5-membered ring and contains, in addition to carbon ring members, from one to three nitrogen atoms, and
$R^3$ is halogen, $C_1$–$C_4$-alkylthio, one of the groups stated for $R^2$ or phenylthio which in turn may carry from one to three of the following radicals: halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, and where the phenylthio group may also carry halogen atoms such that the total number of radicals is 4 or 5,
and salts thereof which can be used in agriculture, are suitable as herbicides.

11 Claims, No Drawings

N-ARYLTETRAHYDROPHTHALIMIDES AND HERBICIDAL COMPOSITIONS THEREOF

The present invention relates to N-aryltetrahydrophthalimides of the formula I

[Structure I: N-aryltetrahydrophthalimide with substituents $R^1$, $R^2$, $R^3$, X]

where
- X is hydrogen or halogen,
- $R^1$ is hydrogen, halogen or $C_1$–$C_4$-alkyl which may carry from one to five halogen atoms;
- $R^2$ is a heteroaromatic structure having a 5-membered ring and containing, in addition to carbon ring members, from one to three nitrogen atoms, the heterocyclic structure being bonded via a nitrogen atom, and
- $R^3$ is halogen, $C_1$–$C_4$-alkylthio, a heteroaromatic structure having a 5-membered ring and containing, in addition to carbon ring members, from one to three nitrogen atoms, this heterocyclic structure being bonded via a nitrogen atom, or phenylthio, which in turn may also carry from one to three of the following radicals: halogen, $C_1$–$C_4$-alkyl, $C_1$–$C_4$-haloalkyl, $C_1$–$C_4$-alkoxy, $C_1$–$C_4$-haloalkoxy or $C_1$–$C_4$-alkylthio, and where the phenylthio group may also carry halogen atoms such that the total number of radicals is 4 or 5, and salts thereof which can be used in agriculture.

The present invention furthermore relates to processes for the preparation of these compounds and to herbicides containing them.

The literature (EP-A 207 894 and EP-A 319 791) discloses N-phenyl-3,4,5,6-tetrahydrophthalimides as herbicidal compounds. The preparation of N-(3-formylphenyl)-3,4,5,6-tetrahydrophthalimides is described in DE-A 38 15 042.

However, the selectivity of the known herbicidal tetrahydrophthalimides with respect to weeds is not entirely satisfactory.

It is an object of the present invention to provide novel herbicidal compounds which permit better and selective control without the crops being significantly damaged.

We have found that this object is achieved by the N-aryltetrahydrophthalimides of the formula I which are defined at the outset.

We have also found a process for the preparation of these N-aryltetrahydro-phthalimides, and herbicides containing them.

The compounds of the formula I in which $R^2$ and $R^3$ are different contain an asymmetric carbon atom and can therefore occur as enantiomers. The racemates can be separated by known methods, for example by salt formation with an optically active acid. Suitable active ingredients are both the pure enantiomers and the isomer mixture obtained in the synthesis.

The compounds I can be prepared by various methods. In particular, they are synthesized by the methods described below.

The compounds I in which $R^3$ is halogen are particularly advantageously obtained by a procedure in which a N-(3-formylphenyl)-tetrahydrophthalimide of the general formula II is reacted with a nitrogen-containing heteroaromatic of the general formula III, having a 5-membered ring, in a conventional manner (Tetrahedron Lett. 52 (1979), 5011) in an inert organic solvent in the presence of an inorganic acid halide [Hal].

[Reaction scheme: II + H—$R^2$ $\xrightarrow{\text{[Hal]}}$ I ($R^3$ = Halogen)]

Suitable inorganic acid halides [Hal] are halogenating agents, such as phosphorus oxychloride, thiophosgene, preferably phosgene and thionyl chloride and bromide.

The starting compounds II are known or obtainable in a known manner (DE-A 3 815 042).

The acid halide is preferably used in not less than equimolar amounts, based on the N-(3-formylphenyl)-tetrahydrophthalimide II. The azole component $R^2$—H is used, for example, in twice, preferably in 5–6 times, the molar amount, based on the acid halide.

The reaction is carried out in general at from $-30°$ to $+100°$ C., preferably from $-10°$ to $+50°$ C., in particular from $0°$ to $20°$ C.

Examples of preferred solvents are nitriles, such as acetonitrile, and ethers, such as tetrahydrofuran, diethyl ether and dioxane. Hydrocarbons and chlorohydrocarbons, such as hexane, benzene, toluene, methylene chloride, carbon tetrachloride and mixtures of the stated solvents are particularly preferred.

The reaction is carried out in general at atmospheric pressure, unless a higher pressure, for example up to 5 bar, is advisable owing to readily volatile reactants.

Since the acid halides and the intermediates formed are sensitive to hydrolysis, the reaction is carried out in general under an inert gas atmosphere ($N_2$, Ar).

Compounds of the formula I in which $R^3$ is not halogen are obtained, for example, by a procedure in which an N-(3-azolylmethylphenyl)-tetrahydrophthalimide of the general formula Ia is reacted with a compound of the general formula IV in a conventional manner in an inert organic solvent in the presence of a base.

[Structure Ia ($R^3$ = Halogen)] +

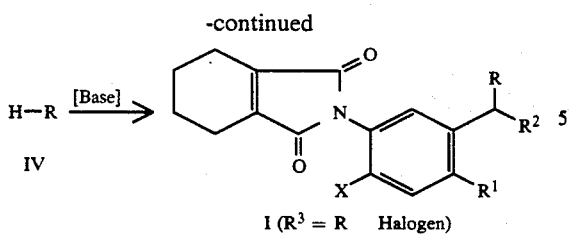

I ($R^3 = R$  Halogen)

In formulae IV and I, R is one of the groups stated for $R^3$ but not halogen. In formula Ia, Hal is halogen, in particular chlorine or bromine.

The compound IV is advantageously used in stoichiometric amounts, preferably in an excess of about 20%, based on Ia.

The reaction is advantageously carried out with the addition of an organic or inorganic auxiliary base and/or of a reaction accelerator in the presence of a solvent.

The amount of base and reaction accelerator can be varied depending on the compound used. A small excess, based on Ia, of the base is advantageously used.

Examples of suitable bases are alkali metal hydroxides, such as lithium hydroxide, sodium hydroxide or potassium hydroxide, alkali metal carbonates or bicarbonates, such as sodium carbonate, potassium carbonate, sodium bicarbonate or potassium bicarbonate, alkali metal amides, such as sodium amide or potassium amide, and the organic bases pyridine, 4-dialkylaminopyridines and dialkylanilines.

The reaction accelerator is preferably added in catalytic amounts to the reaction mixture, preferably in an amount of from 0.001 to 0.1, in particular from 0.01 to 0.05, mole equivalent, based on Ia.

Examples of suitable reaction accelerators are metal halides, preferably sodium iodide or potassium iodide, quaternary ammonium salts, such as tetraalkylammonium halides or bisulfates, preferably tetrabutylammonium halides, such as benzyltriethylammonium chloride or bromide, and crown ethers, such as 12-crown-4, 15-crown-5, benzo-15-crown-5, dibenzo-18-crown-6 or dicyclohexano-18-crown-6.

Preferably used solvents are ketones, such as acetone, methyl ethyl ketone or cyclohexanone, nitriles, such as acetonitrile or propionitrile, alcohols, such as methanol, ethanol, isopropanol, n-butanol or glycols, esters, such as methyl acetate, ethyl acetate or butyl acetate, ethers, such as tetrahydrofuran, diethyl ether or dimethoxyethane, dioxane or diisopropyl ether, amides, such as dimethylformamide, dimethylacetamide or N-methylpyrrolidone, and dimethyl sulfoxide, sulfolane and mixtures of the stated solvents.

The reaction is advantageously carried out at from 0° to 180° C., preferably at the boiling point of the solvent used or of the mixture.

Regarding the pressure, the data for the preparation of the compound Ia are applicable.

The novel processes for the preparation of substituted N-aryltetrahydrophthalimides of the formula I can be carried out continuously or batchwise.

Suitable agriculturally useful salts of the compounds I are the salts of acids which do not adversely affect the herbicidal action, for example the hydrochlorides and hydrobromides, sulfates, nitrates, phosphates, oxalates and dodecylbenzenesulfonates, and metal complexes, such as the complexes of copper, of zinc, of tin, of manganese, of iron, of cobalt or of nickel. The complexes are advantageously prepared from the free nitrogen bases I with salts, for example the chlorides or sulfates, of the corresponding metals with mineral acids.

With regard to the biological activity, important N-aryltetrahydro-phthalimides I are those in which the substituents nave the following meanings:

X is hydrogen or halogen, such as fluorine, chlorine, bromine or iodine, in particular fluorine or chlorine;

$R^1$ is branched or straight-chain alkyl, such as methyl, ethyl, propyl, 1-methylethyl, butyl, 1-methylpropyl, 2-methylpropyl or 1,1-dimethylethyl, in particular methyl, ethyl, propyl or 1-methylethyl; haloalkyl, such as fluoromethyl, difluoromethyl, trifluoromethyl, chlorodifluoromethyl, dichlorofluoromethyl, trichloromethyl, 1-fluoroethyl, 2-fluoroethyl, 2,2-difluoroethyl, 2,2,2-trichloroethyl, 2-chloro-2,2-difluoroethyl, 2,2-dichloro-2-fluoroethyl, 2,2,2-trichloroethyl or pentafluoroethyl, in particular trifluoromethyl, or one of the groups stated for X, in particular hydrogen, fluorine, chlorine or bromine;

$R^2$ is a 5-membered heteroaromatic structure which is bonded via its nitrogen atom and has from one to three nitrogen atoms, such as 1,2-diazol-1-yl, 1,3-diazol-1-yl, 1,2,4-triazol-1-yl, 1,3,4-triazol-1-yl or 1-pyrrolyl, and $R^3$ is halogen as stated for X, in particular chlorine or bromine;

alkythio, such as methylthio, ethylthio, propylthio, 1-methylethylthio, butylthio, 1-methylpropylthio, 2-methylpropylthio or 1,1dimethylethylthio, in particular methylthio, ethylthio, 1-methylethylthio or 1,1-dimethylethylthio;

one of the groups stated for $R^2$, in particular 1,2-diazol-1-yl or phenylthio, where the phenyl ring in turn may also carry from one to three of the following radicals: halogen as stated for X, in particular fluorine, chlorine or bomine;

straight-chain or branched alkyl as stated for $R^1$, in particular methyl, ethyl or 1-methylethyl;

partially or completely halogenated alkyl as stated for $R^1$, in particular difluoromethyl or trifluoromethyl;

alkoxy, such as methoxy, ethoxy, propoxy, 1-methylethoxy, butoxy, 1-methylpropoxy, 2-methylpropoxy or 1,1-dimethylethoxy, in particular methoxy, ethoxy or 1-methylethoxy; partially or completely halogenated alkoxy, such as difluoromethoxy, trifluoromethoxy, chlorodifluoromethoxy, 2,2-difluoroethoxy, 1,1,2,2-tetrafluoroethoxy, 2,2,2-trifluoroethoxy, 2-chloro-1,1,2-trifluoroethoxy or pentafluoroethoxy, in particular trifluoromethoxy or pentafluoroethoxy; or alkylthio as stated above, in particular methylthio or ethylthio, and where the phenyl group may also carry halogen atoms as stated above, in particular fluorine and chlorine, such that the total number of radicals is 4 or 5.

Examples of particularly preferred N-aryltetrahydrophthalimides of the formula I are shown in the Table below.

TABLE I

[Structure: N-aryltetrahydrophthalimide with substituents X, R¹, R², R³]

| X | R¹ | R² | R³ |
|---|----|----|----|
| H | Cl | 1,2,4-Triazolyl | Cl |
| H | Cl | 1,2,4-Triazolyl | SCH₃ |
| H | Cl | 1,2,4-Triazolyl | Br |
| H | Cl | 1,2,4-Triazolyl | SC₄H₉ |
| H | Cl | 1,2,4-Triazolyl | SC₆H₅ |
| H | Cl | 1,2,4-Triazolyl | S–C₆H₄–Cl |
| H | Cl | 1,2,4-Triazolyl | S–C₆H₄–CH₃ |
| H | Cl | 1,2,4-Triazolyl | S–C₆H₄–OCH₃ |
| H | Cl | 1,2,4-Triazolyl | S–C₆H₄–CF₃ |
| H | Cl | 1,2,4-Triazolyl | Pyrazolyl |
| F | Cl | 1,2,4-Triazolyl | Cl |
| F | Cl | 1,2,4-Triazolyl | Br |
| F | Cl | 1,2,4-Triazolyl | SCH₃ |
| F | Cl | 1,2,4-Triazolyl | SC₄H₉ |
| F | Cl | 1,2,4-Triazolyl | SC₆H₅ |
| F | Cl | 1,2,4-Triazolyl | S–C₆H₄–Cl |
| F | Cl | 1,2,4-Triazolyl | S–C₆H₄–F |
| Cl | Cl | 1,2,4-Triazolyl | Cl |
| Cl | Cl | 1,2,4-Triazolyl | Br |
| Cl | Cl | 1,2,4-Triazolyl | SCH₃ |
| F | CF₃ | 1,2,4-Triazolyl | Br |
| Cl | H | 1,2,4-Triazolyl | Cl |
| Cl | H | 1,2,4-Triazolyl | Br |
| Cl | F | 1,2,4-Triazolyl | Cl |
| Cl | F | 1,2,4-Triazolyl | Br |
| Cl | CH₃ | 1,2,4-Triazolyl | Cl |
| Cl | CH₃ | 1,2,4-Triazolyl | Br |
| H | H | Imidazolyl | Cl |
| H | H | Imidazolyl | Br |
| H | F | Imidazolyl | Cl |
| H | F | Imidazolyl | Br |
| H | Cl | Imidazolyl | Cl |
| H | Cl | Imidazolyl | Br |
| H | Cl | Imidazolyl | SCH₃ |
| H | CH₃ | Imidazolyl | Cl |
| H | CF₃ | Imidazolyl | Cl |
| F | H | Imidazolyl | Cl |
| F | F | Imidazolyl | Cl |
| F | Cl | Imidazolyl | Cl |
| F | CH₃ | Imidazolyl | Cl |
| F | CF₃ | Imidazolyl | Cl |
| Cl | H | Imidazolyl | Cl |
| Cl | F | Imidazolyl | Cl |
| Cl | Cl | Imidazolyl | Cl |
| Cl | CH₃ | Imidazolyl | Cl |
| H | H | Pyrazolyl | Cl |
| H | F | Pyrazolyl | Cl |
| H | F | Pyrazolyl | Pyrazolyl |
| H | Cl | Pyrazolyl | Pyrazolyl |
| H | CH₃ | Pyrazolyl | Pyrazolyl |
| H | CF₃ | Pyrazolyl | Pyrazolyl |
| F | H | Pyrazolyl | Pyrazolyl |
| F | F | Pyrazolyl | Pyrazolyl |
| F | Cl | Pyrazolyl | Pyrazolyl |
| F | CH₃ | Pyrazolyl | Pyrazolyl |
| F | CF₃ | Pyrazolyl | Pyrazolyl |
| Cl | H | Pyrazolyl | Pyrazolyl |
| Cl | F | Pyrazolyl | Pyrazolyl |
| Cl | Cl | Pyrazolyl | Pyrazolyl |
| Cl | CH₃ | Pyrazolyl | Pyrazolyl |

The N-aryltetrahydrophthalimides I are suitable as herbicides, in particular for controlling Gramineae species (grasses).

The novel herbicidal compounds I or the agents containing them can be used, for example, in the form of directly sprayable solutions, powders, suspensions, including highly concentrated aqueous, oil or other suspensions or dispersions, emulsions, oil dispersions, pastes, dusting agents, broadcasting agents or granules, by spraying, atomizing, dusting, broadcasting or pouring. The application forms depend on the intended uses; they should in any case ensure very fine distribution of the novel active ingredients.

The compounds I are suitable generally for the preparation of directly sprayable solutions, emulsions, pastes. or oil dispersions. Suitable inert additives are mineral oil fractions having a medium to high boiling point, such as kerosene or diesel oil, and coal tar oils and oils of animal or vegetable origin, aliphatic, cyclic and aromatic hydrocarbons, e.g. toluene, xylene, paraffin, tetrahydronaphthalene, alkylated naphthalenes or derivatives thereof, methanol, ethanol, propanol, butanol, cyclohexanol, cyclohexanone, chlorobenzene, isophorone or strongly polar solvents, such as N,N-dimethylformamide, dimethyl sulfoxide, N-methylpyrrolidone or water.

Aqueous application forms can be prepared from emulsion concentrates, dispersions, pastes, wettable powders or water-dispersible granules by adding water. For the preparation of emulsions, pastes or oil dispersions, the substrates, as such or dissolved in an oil or solvent, can be homogenized in water by means of wetting agents, adherents, dispersants or emulsifiers. However, concentrates which consist of active substance, wetting agents, adherents, dispersants or emulsifiers and possibly solvents or oil and which are suitable for dilution in water can also be prepared.

Suitable surfactants are alkali metal, alkaline earth metal and ammonium salts of aromatic sulfonic acids, for example lignin-, phenol-, naphthalene- and dibutylnaphthalenesulfonic acid, and of fatty acids, alkyl- and alkylarylsulfonates, alkylsulfates, arylethersulfates and fatty alcohol sulfates, and salts of sulfated hexa-, hepta- and octadecanols and of fatty alcohol glycol ethers, condensates of sulfonated naphthalene and its derivatives of formaldehyde, condensates of naphthalene or of the naphthalenesulfonic acids with phenol and formaldehyde, polyoxyethylene octylphenol ethers, ethoxylated isooctyl-, octyl or nonylphenol, alkylphenol polyglycol ethers, tributylphenyl polyglycol ethers, alkylaryl polyether alcohols, isotridecyl alcohol, fatty alcohol/ethylene oxide condensates, ethoxylated castor oil, polyoxyethylene alkyl ethers or polyoxypropylene, lauryl alcohol polyglycol ether acetal, sorbitol esters, ligninsulfite waste liquors or methylcellulose.

Powders, broadcasting agents and dusting agents can be prepared by mixing or milling the active substances together with a solid carrier.

Granules, for example coated, impregnated and homogeneous granules, can be prepared by binding the active ingredients to solid carriers. Solid carriers are mineral earths, such as silica gel, silicas, silicates, talc, kaolin, limestone, lime, chalk, bole, loess, clay, dolomite, kieselguhr, calcium sulfate, magnesium sulfate, magnesium oxide, milled plastics, fertilizers, such as ammonium sulfate, ammonium phosphate, ammonium nitrate or ureas, and vegetable products, such as grain flours, bark meal, wood meal and nutshell meal, cellulosic powders and other solid carriers.

The formulations contain from 0.02 to 95,preferably from 0.5 to 90, % by weight of active ingredient. The active ingredients are used in a purity of from 90 to 100%, preferably from 95 to 100% (according to the NMR spectrum).

The novel compounds I can be formulated, for example, as follows: |90 parts by weight of compound No. 1.007 are mixed with 10 parts by weight of N-methyl-=-pyrrolidone, and a solution which is suitable for use in the form of very small drops is obtained.

II. 20 parts by weight of compound No. 1.003 are dissolved in a mixture which consists of 80 parts by weight of xylene, 10 parts by weight of the adduct of from 8 to 10 moles of ethylene oxide with 1 mole of oleic acid N-monoethanolamide, 5 parts by weight of the calcium salt of dodecylbenzenesulfonic acid and 5 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

III. 20 parts by weight of compound No. 1.002 are dissolved in a mixture which consists of 40 parts by weight of cyclohexanone, 30 parts by weight of isobutanol, 20 parts by weight of the adduct of 7 moles of ethylene oxide with 1 mole of isooctylphenol and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of the active ingredient is obtained.

IV. 20 parts by weight of the active ingredient 1.008 are dissolved in a mixture which consists of 25 parts by weight of cyclohexanone, 65 parts by weight of a mineral oil fraction boiling within the range from 210° to 280° C. and 10 parts by weight of the adduct of 40 moles of ethylene oxide with 1 mole of castor oil. By pouring the solution into 100,000 parts by weight of water and finely distributing it therein, an aqueous dispersion which contains 0.02% by weight of active ingredient is obtained.

V. 20 parts by weight of active ingredient No. 1.001 are thoroughly mixed with 3 parts by weight of the sodium salt of diisobutylnaphthalene-α-sulfonic acid, 17 parts by weight of the sodium salt of a ligninsulfonic acid obtained from a sulfite waste liquor and 60 parts by weight of silica gel powder, and the mixture is milled in a hammer mill. By finely distributing the mixture in 20,000 parts by weight of water, a spray liquor which contains 0.1% by weight of the active ingredient is obtained.

VI. 3 parts by weight of active ingredient No. 1.006 are mixed with 97 parts by weight of finely divided kaolin. A dusting agent which contains 3% by weight of the active ingredient is obtained in this manner.

VII. 30 parts by weight of active ingredient No. 1.003 are thoroughly mixed with a mixture of 92 parts by weight of silica gel powder and 8 parts by weight of liquid paraffin which was sprayed onto the surface of the silica gel. A formulation of the active ingredient having good adhesion is obtained in this manner.

VIII. 20 parts by weight of active ingredient No. 1.005 are thoroughly mixed with 2 parts by weight of the calcium salt of dodecylbenzenesulfonic acid, 8 parts by weight of a fatty alcohol polyglycol ether, 2 parts by weight of the sodium salt of a phenol/urea/formaldehyde condensate and 68 parts by weight of a paraffinic mineral oil. A stable oily dispersion is obtained.

The herbicides or the active ingredients can be applied by the preemergence or postemergence method. If the active ingredients are not very well tolerated by certain crops, it is possible to use application methods in which the herbicides are sprayed with the aid of the sprayers in such a way that, as far as possible, the herbicides do not come into contact with the leaves of the sensitive crops while the active ingredients reach the leaves of undesirable plants growing underneath or the uncovered soil surface (post-directed, lay-by).

The application rates of herbicidal active ingredient are from 0.001 to 3.0, preferably from 0.01 to 2.0, kg/ha of active substance (a.s.), depending on the aim of control, the season, the target plants and the state of growth.

In view of the versatility of the application methods, the novel compounds or agents containing them can be used in a large number of crops for eliminating undesirable plants. For example, the following crops are suitable:

| Botanical name | Common name |
| --- | --- |
| *Allium cepa* | onions |
| *Ananas comosus* | pineapples |
| *Arachis hypogaea* | peanuts (groundnuts) |
| *Asparagus officinalis* | asparagus |
| *Beta vulgaris* spp. *altissima* | sugarbeets |
| *Beta vulgaris* spp. *rapa* | fodder beets |
| *Brassica napus* var. *napus* | rapeseed |
| *Brassica napus* var. *napobrassica* | swedes |
| *Brassica rapa* var. *silvestris* | beets |
| *Camellia sinensis* | tea plants |
| *Carthamus tinctorius* | safflower |
| *Carya illinoinensis* | pecan trees |
| *Citrus limon* | lemon trees |
| *Citrus sinensis* | orange trees |
| *Coffea arabica* (*Coffea canephora, Coffea liberica*) | coffee plants |

| Botanical name | Common name |
| --- | --- |
| Cucumis sativus | cucumbers |
| Cynodon dactylon | Bermudagrass in turf and lawns |
| Daucus carota | carrots |
| Elaeis guineensis | oil palms |
| Fragaria vesca | strawberries |
| Glycine max | soybeans |
| Gossypium hirsutum (Gossypium-arboreum, Gossypium herbaceum, Gossypium vitifolium) | cotton |
| Helianthus annuus | sunflowers |
| Hevea brasiliensis | rubber plants |
| Hordeum vulgare | barley |
| Humulus lupulus | hops |
| Ipomoea batatas | sweet potatoes |
| Juglans regia | walnut trees |
| Lens culinaris | lentils |
| Linum usitatissimum | flax |
| Lycopersicon lycopersicum | tomatoes |
| Malus spp. | apple trees |
| Manihot esculenta | cassava |
| Medicago sativa | alfalfa (lucerne) |
| Musa spp. | banana plants |
| Nicotiana tabacum (N. rustica) | tobacco |
| Olea europaea | olive trees |
| Oryza sativa | rice |
| Phaseolus lunatus | limabeans |
| Phaseolus vulgaris | snapbeans, green beans, dry beans |
| Picea abies | Norway spruce |
| Pinus spp. | pine trees |
| Pisum sativum | English peas |
| Prunus avium | cherry trees |
| Prunus domestica | plum trees |
| Prunus persica | peach trees |
| Pyrus communis | pear trees |
| Ribes sylvestre | redcurrants |
| Ricinus communis | castor-oil plants |
| Saccharum officinarum | sugar cane |
| Secale cereale | rye |
| Solanum tuberosum | Irish potatoes |
| Sorghum bicolor (s. vulgare) | sorghum |
| Theobroma cacao | cacao plants |
| Trifolium pratense | red clover |
| Triticum aestivum | wheat |
| Triticum durum | durum wheat |
| Vicia faba | tick beans |
| Zea mays | Indian corn, sweet corn, maize |

To extend the action spectrum and to achieve synergistic effects, the novel compounds I can be mixed with many typical substances of other groups of herbicidal or growth-regulating active ingredients and applied together with them. Examples of suitable components for the mixture are diazines, 4H-3,1-benzoxazine derivatives, benzothiadiazinones, 2,6-dinitroanilines, N-phenylcarbamates, thiolcarbamates, halo carboxylic acids, triazines, amides, ureas, diphenyl ethers, triazinones, uracils, benzofuran derivatives, cyclohexane-1,3-dione derivatives, quinolinecarboxylic acid derivatives, aryloxy- and hetaryloxyphenoxypropionic acids and their salts, esters and amides and others.

It may also be useful if the compounds I, alone or in combination with other herbicides, are also applied as a mixture together with further crop protection agents, for example with pesticides or agents for controlling phytopat-hogenic fungi or bacteria. The miscibility with mineral salt solutions which are used for eliminating nutrient and trace element deficiencies is also of interest. Nonphytotoxic oils and oil concentrates may also be added.

Examples of Syntheses

The methods described in the following Examples of Syntheses were used for obtaining further compounds I, with appropriate modification of the starting compounds. The compounds thus obtained are shown in the Table below, together with physical data.

EXAMPLE 1

N-[3-(Chloro-1,2,4-triazol-1-ylmethyl)-4-chlorophenyl]-3,4,5,6-tetrahydrophthalimide

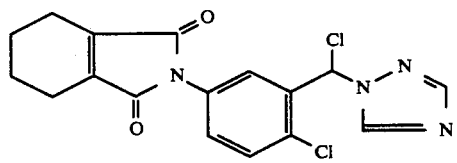

6.2 g of thionyl chloride were added to a solution of 14.3 g of triazole in 100 ml of methylene chloride at 0° C. under a nitrogen atmosphere, followed, after stirring for 30 minutes at 25° C., by 10 g (0.027 mol) of N-(3-formyl-4-chlorophenyl)-3,4,5,6-tetrahydrophthalimide.

After a reaction time of 12 hours at 25° C., 100 ml of water were added, after which the isolated aqueous phase was extracted twice with methylene chloride. The combined organic phases were then worked up in a conventional manner to obtain the azolylmethyl derivative. Recrystallization from methyl tert-butyl ether gave 9.7 g of the product.

Yield: 97%; mp. 128°-131° C.

(Active Ingredient Example 1.001)

EXAMPLE 2

N-[3-Methylthio-1,2,4-triazol-1-ylmethyl)-4-chlorophenyl]-3,4,5,6-tetrahydrophthalimide

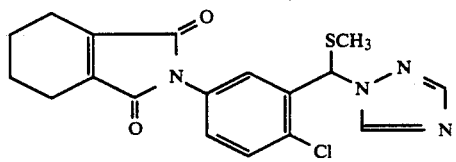

A solution of 3 g (0.008 mole) of N-[3-(chloro 1,2,4-triazol-1-ylmethyl)-4-chlorophenyl]-3,4, 5,6-tetrahydrophthalimide (Example 1) in 50 ml of N,N-dimethylformamide, 0.6 g of sodium methanethiolate and a pinch of potassium iodide were heated at 50° C. for 12 hours, after which 100 ml of water were added. After extraction with methyl tert-butyl ether, the organic phase was washed and was worked up in a conventional manner.

Yield: 1.0 g (32%); oil (Active Ingredient Example 1.002)

TABLE 1

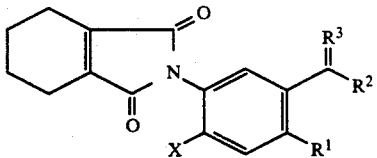

| Example No. | X | R¹ | R² | R³ | Phys. data [Mp. (°C.); IR (cm⁻¹)] |
|---|---|---|---|---|---|
| 1.001 | H | Cl | 1,2,4-Triazolyl | Cl | 128–131 |
| 1.002 | H | Cl | 1,2,4-Triazolyl | SCH₃ | 1713, 1480, 1377 cm⁻¹ |
| 1.003 | H | Cl | 1,2,4-Triazolyl | Br | 120–124 |
| 1.004 | H | Cl | Imidazolyl | Cl | 198–204 |
| 1.005 | H | F | Pyrazolyl | Pyrazolyl | 92–94 |
| 1.006 | H | Cl | Pyrazolyl | Pyrazolyl | 178–180 |
| 1.007 | F | F | Pyrazolyl | Pyrazolyl | 205–207 |
| 1.008 | F | Cl | Pyrazolyl | Pyrazolyl | 192–194 |

Examples of Use

The herbicidal action of the N-aryltetrahydrophthalimides of the formula I can be demonstrated by greenhouse experiments:

The culture vessels used were plastic flowerpots containing loamy sand with about 3.0% of humus as a substrate. The seeds of the test plants were sown separately according to species.

In the preemergence treatment, the active ingredients suspended or emulsified in water were applied directly after sowing, by means of finely distributing nozzles. The vessels were lightly watered in order to promote germination and growth and were then covered with transparent plastic covers until the plants had started to grow. This covering ensures uniform germination of the test plants, unless this has been adversely affected by the active ingredients.

For the purpose of the postemergence treatment, the test plants were treated with the active ingredients suspended or emulsified in water only at a height of growth of from 3 to 15 cm, depending on the form of growth. The application rate for the postemergence treatment was 0.125 kg/ha of a.s.

The plants were kept at 10°–25° C. or 20°–35° C., according to species. The test period extended over from 2 to 4 weeks. During this time, the plants were tended and their reaction to the individual treatments was evaluated.

The evaluation was based on a scale from 0 to 100. 100 means no emergence of the plants or complete destruction of at least the above-ground parts and 0° means no damage or a normal course of growth.

The plants used in the greenhouse experiments consisted of the following species:

| Botanical name | Common name |
|---|---|
| *Abutilon theophrasti* | Chinese hemp |
| *Chenopodium album* | pigweed |
| *Zea mays* | corn |

When 0.125 kg/ha of a.s. is used in the postemergence method, undesirable broad-leaved plants can be very readily controlled with Examples 1.002 and 1.008. Example 1.002 is also well tolerated by the example crop corn.

We claim:

1. An N-aryltetrahydrophthalimide of the formula I where
X is hydrogen or halogen,
R¹ is hydrogen, halogen or C₁–C₄-alkyl which may carry from one to five halogen atoms;
R² is a heteroaromataic structure selected from the group consisting of pyrrolyl, imidazolyl, triazolyl and pyrazolyl, the heterocyclic structure being bonded via a nitrogen atom, and
R³ is halogen, C₁–C₄-alkylthio, a heteroaromatic structure selected from the group consisting of pyrrolyl, imidazolyl, triazolyl and pyrozolyl, this heterocyclic structure being bonded via a nitrogen atom, or phenylthio, which in turn may be substituted by from one to three of the following radicals: C₁–C₄-alkyl, C₁–C₄-haloalkyl, C₁–C₄-alkoxy, C₁–C₄-haloalkoxy or C₁–C₄-alkylthio, or may be substituted by from 1–5 halogen atoms such that the total number of radicals is 4 or 5,
or a salt thereof which can be used in agriculture.

2. A compound of the formula I as defined in claim 1, wherein X is hydrogen, R¹ is Cl, R² is 1,2,4-triazolyl and R³ is Cl.

3. A compound of the formula I as defined in claim 1, wherein X is H, R¹ is Cl, R² is 1,2,4-triazolyl and R³ is SCH₃.

4. A compound of the formula I as defined in claim 1, wherein X is H, R¹ is Cl, R² is 1,2,4-triazolyl and R³ is Br.

5. A compound of the formula I as defined in claim 1, wherein X is H, R¹ is Cl, R² is imidazolyl and R³ is Cl.

6. A compound of the formula I as defined in claim 1, wherein X is H, R¹ is F, R² is pyrozolyl and R³ is pyrazolyl.

7. A compound of the formula I as defined in claim 1, wherein X is H, R¹ is Cl, R² is pyrazolyl and R³ is pyrazolyl.

8. A compound of the formula I as defined in claim 1, wherein X is F, R¹ is F, R² is pyrazolyl and R³ is pyrazolyl.

9. A compound of the formula I as defined in claim 1, wherein X is F, R¹ is Cl, R² is pyrazolyl and R³ is pyrazolyl.

10. A herbicidal composition containing a herbicidal amount of an N-aryltetrahydropthalimide of the formula I as defined in claim 1 and inert additives.

11. A method for controlling undesirable plant growth, wherein the undesirable plants or their habitat are treated with a herbicidal amount of an N-aryltetrahydrophthalimide of the formula I as defined in claim 1.

* * * * *

UNITED STATES PATENT AND TRADEMARK OFFICE
CERTIFICATE OF CORRECTION

PATENT NO.  : 5,133,799
DATED       : July 28, 1992
INVENTOR(S) : Rainier Seele, et. al.

It is certified that error appears in the above-indentified patent and that said Letters Patent is hereby corrected as shown below:

On the Title page, item [30], Foreign Application Priority Data: "May 10" should read "May 11"
On the Title page, item [57], Abstract, before Formula I insert-- N-Aryltetrahydrophthalimides I --.
On the Title page, item [57], Abstract, correct the formula as shown below

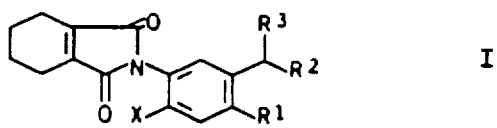

Claim 1, formula I:  correct the formula as shown above
Claim 1, column 12, line 24, "pyrozolyl" should read -- pyrazolyl --
Claim 6, column 12, line 46, "pyrozolyl" should read -- pyrazolyl --
Claim 10, column 12, line 58, "N-aryltetrahydropthalimide" should read -- N-aryltetrahydrophthalimide --.

Signed and Sealed this

Seventeenth Day of August, 1993

Attest:

BRUCE LEHMAN

*Attesting Officer*         *Commissioner of Patents and Trademarks*